(12) United States Patent
Weigel et al.

(10) Patent No.: US 10,711,305 B2
(45) Date of Patent: Jul. 14, 2020

(54) METHOD FOR GENDER IDENTIFICATION IN DOMESTIC CHICKEN

(71) Applicant: DEREGG GMBH, Kiel (DE)

(72) Inventors: Martin Christian Weigel, Kiel (DE); Karsten Hofmann-Peiker, Kiel (DE); Michael Kleine, Kiel (DE)

(73) Assignee: DIREGG GMBH, Kiel (DE)

( * ) Notice: Subject to any disclaimer, the term of this patent is extended or adjusted under 35 U.S.C. 154(b) by 27 days.

(21) Appl. No.: 15/772,842

(22) PCT Filed: Nov. 3, 2016

(86) PCT No.: PCT/EP2016/076526
§ 371 (c)(1),
(2) Date: May 2, 2018

(87) PCT Pub. No.: WO2017/076957
PCT Pub. Date: May 11, 2017

(65) Prior Publication Data
US 2019/0203292 A1    Jul. 4, 2019

(30) Foreign Application Priority Data
Nov. 3, 2015   (EP) .................................... 15192841

(51) Int. Cl.
*C07H 21/04*   (2006.01)
*C12Q 1/68*    (2018.01)
*C12Q 1/6879*  (2018.01)

(52) U.S. Cl.
CPC ..... *C12Q 1/6879* (2013.01); *C12Q 2600/124* (2013.01)

(58) Field of Classification Search
None
See application file for complete search history.

(56) References Cited

U.S. PATENT DOCUMENTS 5,707,809 A    1/1998    Halverson et al.

FOREIGN PATENT DOCUMENTS

| CN | 101130816 | * | 2/2008 | ............... C12Q 1/68 |
|----|-----------|---|--------|---------------------------|
| CN | 101130816 | A | 2/2008 | |
| CN | 102864243 | * | 1/2013 | ............... C12Q 1/68 |
| CN | 103525908 |   | 1/2014 | |
| KR | 1020100020287 | A | 2/2010 | |
| KR | 1020130023909 | A | 3/2013 | |
| WO | WO 2004/016812 |   | 2/2004 | |

OTHER PUBLICATIONS

Rosenthal et al. (Poultry Science, vol. 89,, pp. 1451-1456, 2010) (Year: 2010).*
Aun et al. (Pertanika J. Trop. Agric. Sci, vol. 33, No. 2, pp. 329-336, 2010 (Year: 2010).*

(Continued)

*Primary Examiner* — Jeanine A Goldberg
(74) *Attorney, Agent, or Firm* — Parker Highlander PLLC

(57) ABSTRACT

The present invention relates to a method for the detection of the presence or absence of at least one nucleic acid sequence specific for the sex of chicken using polymerase chain reaction in a high-throughput manner, a kit for conducting the method of the present invention and a pair of oligonucleotides.

21 Claims, 4 Drawing Sheets

Specification includes a Sequence Listing.

| 1   | gaattctata | gataaatagt | gtagtcacta | tgaacttgag | atagtgactt | ccttctggca |
|-----|------------|------------|------------|------------|------------|------------|
| 61  | aagatcctaa | ttcaaaggga | gtatctagca | gttatggtcc | tatgcctacc | acattcctat |
| 121 | ttgctagatg | tctttgatga | ctataatcaa | aacaacatga | aatactaagc | ataagcaatc |
| 181 | atgttaacat | tagggtcact | gaattttact | taaaagtttc | agtgcattta | ttttactgtg |
| 241 | tatttcctgt | ttatccaccc | tagattggtt | aacctattc  | attgacaatt | tatctatctc |
| 301 | caggggaaag | ctgtatacaa | gcaaggaact | aaatcagtgc | caacaacaac | gataaatgtt |
| 361 | ttagaatcac | ctaatgtcg  | gaatgtcaat | tttaactgaa | atccacttca | ggtcagatta |
| 421 | tctctcagac | tcaacctgaa | cccattactt | agaagatggt | ctgaagtcca | gctgaagcac |
| 481 | ttaaaacaca | aagtgaactg | agaggttcct | aaacaaaacg | cattcaaagt | agtagtagtt |
| 541 | tggtttcctt | tcccagaaag | aatgctctga | gtatgtcttc | aaagaattc  | |

(56) References Cited

OTHER PUBLICATIONS

Itoh et al. (The Journal of Heredity, vol. 92, No. 4, pp. 315-321, 2001 (Year: 2001).*
Aun, Richard Teh Swee, and Jayarai Vijaya Kumaran, "Gender identification of domesticated chicken using a PCR-based method." *Pertanika J. Trop. Agric. Sci* 33.2 (2010): 329-336.
Haunshi, Santosh, et al. "A simple and quick DNA extraction procedure for rapid diagnosis of sex of chicken and chicken embryos." *The Journal of Poultry Science* 45.1 (2008): 75-81.
International Search Report and Written Opinion issued in International Application No. PCT/EP2016/076526, dated Jan. 24, 2017.
Ogawa, Akira, et al. "Molecular characterization and cytological mapping of a non-repetitive DNA sequence region from the W chromosome of chicken and its use as a universal probe for sexing Carinatae birds." *Chromosome Research* 5.2 (1997): 93-101.
Rosenthal, N. F., et al. "High-throughput applicable genomic sex typing of chicken by TaqMan real-time quantitative polymerase chain reaction," *Poultry science* 89.7 (2010): 1451-1456.
Weissmann, A., et al. "Sexing domestic chicken before hatch: A new method for in ovo gender identification." *Theriogenology* 80.3 (2013): 199-205.
Fedick, Anastasia, et al. "High-throughput carrier screening using TaqMan allelic discrimination." *PloS One* 8.3 (2013).
Yuan, Jiazheng, et al. "Introduction of high throuhput and cost effective SNP genotyping platforms in soybean." *Plant Genetics, Genoinics, and Biotechnology* 2.1 (2014): 90-94.

* cited by examiner

| | | | | | | |
|---|---|---|---|---|---|---|
| 1 | gaattctata | gataaatagt | gtagtcacta | tgaacttgag | atagtgactt | ccttctggca |
| 61 | aagatcctaa | ttcaaaggga | gtatctagca | gttatggtcc | tatgcctacc | acattcctat |
| 121 | ttgctagatg | tctttgatga | ctataatcaa | aacaacatga | aatactaagc | ataagcaatc |
| 181 | atgttaacat | tagggtcact | gaattttact | taaaagtttc | agtgcattta | ttttactgtg |
| 241 | tatttcctgt | ttatccaccc | tagattggtt | aacctatttc | attgacaatt | tatctatctc |
| 301 | caggggaaag | ctgtatacaa | gcaaggaact | aaatcagtgc | caacaacaac | gataaatgtt |
| 361 | ttagaatcac | ctaatgtgcg | gaatgtcaat | tttaactgaa | atccacttca | ggtcagatta |
| 421 | tctctcagac | tcaacctgaa | cccattactt | agaagatggt | ctgaagtcca | gctgaagcac |
| 481 | ttaaaacaca | aagtgaactg | agaggttcct | aaacaaaacg | cattcaaagt | agtagtagtt |
| 541 | tggtttcctt | tcccagaaag | aatgctctga | gtatgtcttc | aaagaattc | |

Fig. 1

SEQUENCE LISTING

```
<160> NUMBER OF SEQ ID NOS: 16

<210> SEQ ID NO 1
<211> LENGTH: 589
<212> TYPE: DNA
<213> ORGANISM: Artificial sequence
<220> FEATURE:
<223> OTHER INFORMATION: Chicken W chromosome fragment

<400> SEQUENCE: 1
gaattctata gataaatagt gtagtcacta tgaacttgag atagtgactt ccttctggca      60
aagatcctaa ttcaaaggga gtatctagca gttatggtcc tatgcctacc acattcctat     120
ttgctagatg tctttgatga ctataatcaa aacaacatga aatactaagc ataagcaatc     180
atgttaacat tagggtcact gaattttact taaaagtttc agtgcattta ttttactgtg     240
tatttcctgt ttatccaccc tagattggtt aacctatttc attgacaatt tatctatctc     300
caggggaaag ctgtatacaa gcaaggaact aaatcagtgc caacaacaac gataaatgtt     360
ttagaatcac ctaatgtgcg gaatgtcaat tttaactgaa atccacttca ggtcagatta     420
tctctcagac tcaacctgaa cccattactt agaagatggt ctgaagtcca gctgaagcac     480
ttaaaacaca aagtgaactg agaggttcct aaacaaaacg cattcaaagt agtagtagtt     540
tggtttcctt tcccagaaag aatgctctga gtatgtcttc aaagaattc                 589

<210> SEQ ID NO 2
<211> LENGTH: 20
<212> TYPE: DNA
```

```
<213> ORGANISM: Artificial sequence
<220> FEATURE:
<223> OTHER INFORMATION: Forward primer W chromosome GP1GGW_76bp

<400> SEQUENCE: 2
ctaatgtgcg gaatgtcaat                                                 20

<210> SEQ ID NO 3
<211> LENGTH: 20
<212> TYPE: DNA
<213> ORGANISM: Artificial sequence
<220> FEATURE:
<223> OTHER INFORMATION: Reverse primer W chromosome GP2GGW_76bp

<400> SEQUENCE: 3
aatgggttca ggttgagtct                                                 20

<210> SEQ ID NO 4
<211> LENGTH: 20
<212> TYPE: DNA
<213> ORGANISM: Artificial sequence
<220> FEATURE:
<223> OTHER INFORMATION: Forward primer W chromosome GP1GGW_116bp

<400> SEQUENCE: 4
gcagttatgg tcctatgcct                                                 20

<210> SEQ ID NO 5
<211> LENGTH: 22
<212> TYPE: DNA
<213> ORGANISM: Artificial sequence
<220> FEATURE:
<223> OTHER INFORMATION: Reverse primer W chromosome GP2GGW_116bp

<400> SEQUENCE: 5
ttcagtgacc ctaatgttaa ca                                              22

<210> SEQ ID NO 6
<211> LENGTH: 20
<212> TYPE: DNA
<213> ORGANISM: Artificial sequence
<220> FEATURE:
<223> OTHER INFORMATION: Forward primer W chromosome GP1GGW_152bp

<400> SEQUENCE: 6
ctatctccag gggaaagctg                                                 20

<210> SEQ ID NO 7
<211> LENGTH: 20
<212> TYPE: DNA
<213> ORGANISM: Artificial sequence
<220> FEATURE:
<223> OTHER INFORMATION: Reverse primer W chromosome GP2GGW_152bp

<400> SEQUENCE: 7
atgggttcag gttgagtctg                                                 20

<210> SEQ ID NO 8
<211> LENGTH: 20
<212> TYPE: DNA
<213> ORGANISM: Artificial sequence
<220> FEATURE:
<223> OTHER INFORMATION: Forward primer W chromosome GP1GGW_66bp

<400> SEQUENCE: 8
gacttccttc tggcaaagat                                                 20
```

<210> SEQ ID NO 9
<211> LENGTH: 20
<212> TYPE: DNA
<213> ORGANISM: Artificial sequence
<220> FEATURE:
<223> OTHER INFORMATION: Reverse primer W chromosome GP2GGW_66bp

<400> SEQUENCE: 9
tggtaggcat aggaccataa                                              20

<210> SEQ ID NO 10
<211> LENGTH: 15
<212> TYPE: DNA
<213> ORGANISM: Artificial sequence
<220> FEATURE:
<223> OTHER INFORMATION: Forward primer HKG gene GP1Gallus1F

<400> SEQUENCE: 10
cagctggcct gccgg                                                   15

<210> SEQ ID NO 11
<211> LENGTH: 21
<212> TYPE: DNA
<213> ORGANISM: Artificial sequence
<220> FEATURE:
<223> OTHER INFORMATION: Reverse primer HKG gene GP2Gallus1R

<400> SEQUENCE: 11
cccagtggaa tgtggtattc a                                            21

<210> SEQ ID NO 12
<211> LENGTH: 21
<212> TYPE: DNA
<213> ORGANISM: Artificial sequence
<220> FEATURE:
<223> OTHER INFORMATION: Probe W chromosome GS1GGW_76bp

<400> SEQUENCE: 12
actgaaatcc acttcaggtc a                                            21

<210> SEQ ID NO 13
<211> LENGTH: 24
<212> TYPE: DNA
<213> ORGANISM: Artificial sequence
<220> FEATURE:
<223> OTHER INFORMATION: Probe W chromosome GS1GGW_116bp

<400> SEQUENCE: 13
accacattcc tatttgctag atgt                                         24

<210> SEQ ID NO 14
<211> LENGTH: 20
<212> TYPE: DNA
<213> ORGANISM: Artificial sequence
<220> FEATURE:
<223> OTHER INFORMATION: Probe W chromosome GS1GGW_152bp

<400> SEQUENCE: 14
tcagtgccaa caacaacgat                                              20

<210> SEQ ID NO 15
<211> LENGTH: 25
<212> TYPE: DNA
<213> ORGANISM: Artificial sequence
<220> FEATURE:

-continued

```
<223> OTHER INFORMATION: Probe W chromosome GS1GGW_66bp

<400> SEQUENCE: 15
cctaattcaa agggagtatc tagca                                              25

<210> SEQ ID NO 16
<211> LENGTH: 23
<212> TYPE: DNA
<213> ORGANISM: Artificial sequence
<220> FEATURE:
<223> OTHER INFORMATION: Probe HKG gene GS1Gallus1

<400> SEQUENCE: 16
tctgccactc ctctgcaccc agt                                                23
```

METHOD FOR GENDER IDENTIFICATION IN DOMESTIC CHICKEN

This application is a national phase application under 35 U.S.C. § 371 of International Application No. PCT/EP2016/076526, filed Nov. 3, 2016, which claims benefit of priority to European Application No. 15192841.3, filed Nov. 3, 2015, the entire contents of each of which are hereby incorporated by reference.

The present invention relates to a method for the detection of the presence or absence of at least one nucleic acid sequence specific for the sex of chicken using polymerase chain reaction, a kit for conducting the method of the present invention and a pair of oligonucleotides.

Keeping laying hens requires the determining of sex in order to sort out the male offspring. Conventional procedures foresee that the male chicks are sort out and subsequently killed after the hatch. The common practice to kill the male chicks includes among other methods the treatment with carbon dioxide. These methods are currently under debate because of ethical concerns.

At present, the determining of sex—sexing—is conducted by the very wildly used technique of cloacal sexing. However, the accuracy rate of this technique is fairly low due to several factors such as morphological variation of the sexual organs in different species or the individual experience of the person conducting the cloacal sexing.

A further method allows the determination of estradiol, estrone sulfate, and testosterone in allantoic fluid (Weissmann et al., Theriogenology, 2013 August; 80(3):199-205.). This method allows the sex determination in ovo on days 7 to 10 of incubation. The determination of sex hormones is conducted in form of an enzyme immunoassay. Conducting of this immune assay however provides only low precision and specificity. A further disadvantage of this method is that the determination of sex is only predictable not before 7 days of incubation. Further, the assay allows only the assessment of different concentrations of hormones which are characteristic for gender discrimination. However, this immunoassay does not represent an assay which provides a definite read-out system which gives the signal for an unambiguous positive or negative result. Moreover, it is necessary to take out a relative large amount of fluid out of the egg. This however, may have a negative influence on the success of the following hatch.

Ogawa et al., Chromosome Research 1997, 5, 93-101 identified a genomic DNA region from the W chromosome of chicken. This DNA region allows that the female sex can be determined by polymerase chain reaction (PCR) in form of an unambiguous female-specific band in the resulting analysis of the PCR products.

Further, Aun and Kumaran, Pertanika J. Trop. Agric. Sci. 33 (2): 329-336, 2010 describe a PCR based gender determination protocol which should provide a higher accuracy rate than conventional sexing methods. Nevertheless, this protocol is not efficient to be suitable for high-throughput analysis and automatization.

Rosenthal et al., 2010 Poultry Science 89: 1451-1456 describe a protocol of chicken genetic sex typing by TaqMan real-time quantitative PCR amplification of markers on the sex chromosomes. However, this PCR has been shown to be not sensitive enough. Therefore, this assay is also not suitable for high-throughput analysis and automatization.

The laying hens industry is under financial pressure, such that it is not desired to raise the male chicken offspring in order to avoid any additional costs for food, water or medical treatment, such as vaccination. Further, it is not intended to keep the male chicken, since these are of course not useful for laying eggs and further are not capable to be used for meat production. The meat production is conducted with chicken of different varieties compared to the chicken varieties used for laying eggs.

In view of the above-mentioned drawbacks and necessities, the present invention underlies the technical problem to provide an improved method in respect of reliability, preciseness, robustness, high-throughput analysis and automatization demands for the determination of sex in domestic chicken in hatcheries.

The present invention overcomes the drawbacks of the methods of the prior art and provides as solution for the underlying technical problem an improved method for the determination of sex in domestic chicken which method relies on the detection of distinct nucleic sequences specific for chicken's W chromosome.

The technical solution of the present invention is in particular defined in the subject-matter of the claims.

The invention is further illustrated in the following figures.

FIG. 1 shows the sequence according to SEQ ID NO:1 representing a chicken W chromosome fragment. Underlined with a black line is the range of nucleotide 46 to 446.

Figure 2:
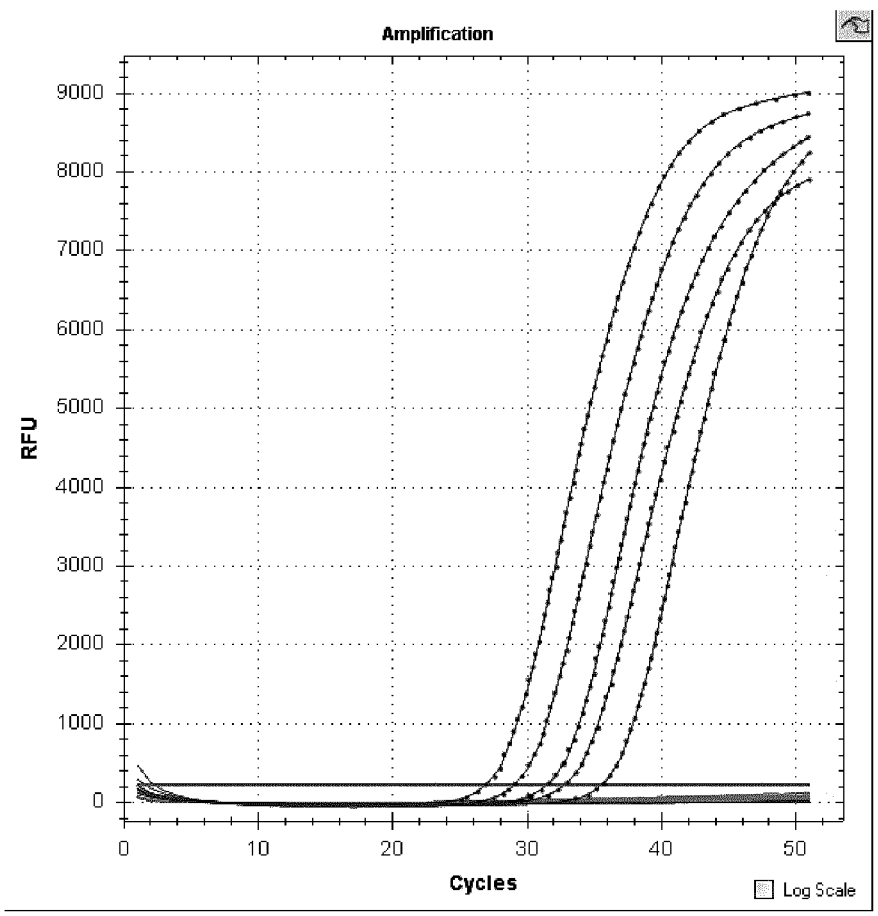
FIG. 2 shows the result of a real-time PCR. Male chicken DNA is depicted in different concentrations.

In the context of the present invention the term "PCR" relates to polymerase chain reaction which is a procedure of target amplification. The term "target amplification" relates to an enzyme-mediated procedure which is capable of producing billions of copies of nucleic acid target sequences. PCR as particular target amplification method is well known to those of ordinary skill in the art. In general, conducting PCR foresees that a sample of DNA is mixed in a solution with at least two oligonucleotide primers that are prepared to be complementary to each strand of the DNA duplex. Nucleotide bases—dNTPs—and a DNA polymerase, such as Taq polymerase, are used to catalyze the formation of DNA from the oligonucleotide primers and the dNTPs. At least one of the primers is a so called forward primer binding in 5' to 3' direction to the 3' end of the first strand of the DNA; the so called reverse primer is binding in 3' to 5' direction to the 5' end of the second strand of the DNA. The general principle of the PCR procedure foresees that the solution is heated to denature the double-stranded DNA to single-stranded DNA. After cooling down of the solution to the so called annealing temperature, the primers are able to bind to the separated DNA strands and the DNA polymerase catalyzes the generation of a new strand by joining the dNTPs to the primers. This process is repeated in several cycles resulting in a respective amount of amplified PCR products.

The term "real-time PCR" relates to the detection of PCR products via fluorescence signals which are generated by cleavage of a dual labeled probe during hybridization of the PCR product. A dual labeled probe has a fluorescence dye and a quencher moiety. Examples of commonly used probes are TAQMAN® probes.

The term "primer" in the context of the present invention relates to oligonucleotide sequences of between 10 and 30 nucleotides in length. The term "primer" relates also to an oligonucleotide that is capable of providing a point of initiation for the 5' to 3' synthesis, the result of this synthesis—the primer extension product—being complementary to a nucleic acid strand. The primer extension product is generally synthesized in the presence of appropriate nucleotides and an agent for polymerization such as a DNA polymerase in an appropriate buffer and at a suitable temperature. According to the present invention, oligonucleotide sequences of the primers are between 10 to 30 nucleotides, for example any range between 10 and 30 nucleotides, such as between 10 and 25 nucleotides, between 15 and 30 nucleotides, between 18 and 25 nucleotides, between 18 and 30 nucleotides, between 10 and 20 nucleotides, or between 15 and 20 nucleotides etc.

The term "probe" according to the present invention relates to an oligonucleotide that forms a hybrid structure with a target sequence contained in a molecule in a sample undergoing analysis, due to the complementarity of at least one sequence in the probe with the target sequence. According to the present invention, oligonucleotide sequences of the probes are between 15 to 40 nucleotides, for example any range between 15 and 40 nucleotides, such as between 15 and 30 nucleotides, between 15 and 25 nucleotides, between 18 and 25 nucleotides, between 18 and 30 nucleotides, between 10 and 20 nucleotides, or between 15 and 20 nucleotides etc.

The term "W chromosome" according to the present invention relates to the W chromosome or fragments of the W chromosome. In the context of the present invention, the term "W chromosome" relates to a particular fragment of the W chromosome as described in Ogawa et al., Chromosome Research 1997, 5, 93-101. In particular, the term "W chromosome" relates to W chromosome of chicken. Moreover, the term "W chromosome" can also relate to the W chromosome of Carinatae birds in general, including the group of all birds and their extinct relatives to possess a keel, or "carina", on the underside of the breastbone used to anchor large flight muscles. Thus, Carinatae birds may include for example white leghorn chicken, domestic turkey, or domestic duck.

The term "HKG" in the context of the present invention relates to a House Keeping Gene of Gallus. This gene is described in Koppel et al., Eur Food Res Technol (2010) 230:367-374. The detection of the HKG allows the determination of a positive conduction of the PCR in the context of the present invention. In particular, the detection of HKG allows determining the presence of male chicken DNA.

A first subject-matter of the present invention relates to a method for the detection of the presence or absence of at least one nucleic acid sequence specific for the sex of chicken in a biological sample using polymerase chain reaction (PCR), wherein the method comprises the following steps of: (a) providing a nucleic acid sequence from the biological sample, (b) amplifying and detecting at least one target sequence specific for the sex of chicken using PCR, wherein a forward primer and a reverse primer is used, the forward primer and the reverse primer each comprises an oligonucleotide of between 10 and 30 nucleotides in length and of at least 10 contiguous nucleotides of a nucleotide sequence located in the range of nucleotide 46 to 446 of SEQ ID NO:1, and wherein the target sequence has a size in the range of about 70 base pairs (bp) to 160 bp, wherein the nucleic acid sequence specific for the sex of chicken is a sequence of the W chromosome of chicken.

The inventors could have shown that a reliable determination of the female chicken W chromosome can be conducted if forward and reverse primer are selected from a distinct nucleotide range from nucleotide 46 to 446 of SEQ ID NO: 1. SEQ ID NO:1 represents a female specific sequence of the W chromosome as described in Ogawa et al., Chromosome Research 1997, 5, 93-101. The inventors were able to provide a reliable, precise and robust method for the determination of the sex in chicken on the basis of the application of a PCR using distinct primers which are located in said region from nucleotide 46 to 446 of SEQ ID NO: 1. The method of the present invention has the advantages that already only 1 to 3 genome copies from the starting biological material is sufficient to allow the gender discrimination and to predict the presence of female chicks. Accordingly, it is possible to determine already at a very early point in time already from day 3 on or later after the incubation of the egg.

A further advantage of the method of the present invention is that the product size of the amplification product is relative small with 70 to 160 bp. Such an amplification product size allows also an improved productivity, sensitivity and specificity of the PCR. A further advantage of such a small amplification product is the fact that the generation of unwanted secondary structures is inhibited and thus a high sensitivity can be achieved. It has also to note that in contrast to the set of primer as described in Ogawa et al., 1997 the present method of the invention foresees to use the exact target sequence and not the provision of a degenerated system.

According to the above, the product size of the amplification product, which means the target sequence of the method of the present invention, is a crucial factor for a reliable detection method in a high-throughput application. The relation between the length of the amplification product, which means the PCR product or amplicon size and the sensitivity, productivity and specificity of the PCR is an important factor. On the one hand, a PCR assay with an amplicon too short (<70 bp) in size tends to be unspecific. This means, that under low copy number conditions (<3) of the template false positive signals occur. On the other hand, an enlargement of the amplicon size (>160 bp) reduces the productivity of the PCR, so that the probability to detect 1-3 copies of the target sequence will decrease significantly. As a consequence, only a limited and well-defined size of the PCR amplicon allows a reliable gender determination such as from allantois liquid in an early embryogenic developmental stage.

Moreover, in the case of the determination of a target sequence on the basis of biological material obtained from the egg to conduct the gender identification, it has to be noted that usually only a small amount of DNA material is available. The reason for this is that only a minor amount of biological material and thus a minor amount of source DNA in this early developmental stage can be obtained from the egg to avoid any serious damage of the embryo which may then lead to an abort of the further hatching process. Thus, the amplification of a target sequence of larger size would require a greater amount of source DNA, which is however not available due to the reasons as mentioned above.

Therefore, the inventors identified that a target sequence size in the range of about 70 bp to 160 bp provides very specific, sensitive and reliable results in the method for the detection according to the present invention. Specific, sensitive and reliable results are important for the application of the method in large scale format, such as high-throughput format. Advantageously, the method according to the present invention is able to provide reliable and specific and sensitive results even with very low amount of source material, such as only 1 to 3 gene copies. In contrast to this, the methods described in the prior art are directed to larger product sizes of the amplification products, such as amplification products of a size of greater than 240 bp. However, in view of the requirements to provide a method which is also suitable to provide reliable and sensitive results on the basis of low amount of source DNA, these known methods fail to fulfill these demands.

In a preferred embodiment of the present invention, the target sequence has a size in the range of about 75 bp to 155 bp, preferably of about 75 bp to 140 bp, preferably of about 75 bp to 120 bp, further preferred of about 75 bp to 100 bp, in particular preferred of about 76 bp. In accordance with the present invention, it is foreseen that any intermediate range of the size of the target sequence is preferred within the range of 70 bp to 160 bp. In a certain particular preferred embodiment the target sequence has a size of 76 bp. Further certain preferred embodiments comprise a size of the target sequence of 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, or greater up to a size of the target sequence of 160 bp, or at least any intermediate size of the target sequence between one of the specifically recited sizes, or within any range of sizes.

In a further preferred embodiment of the present invention, the forward primer is selected from the group consisting of SEQ ID NO: 2, 4, 6, and 8, and the reverse primer is selected from the group consisting of SEQ ID NO: 3, 5, 7, and 9.

According to the present invention it is foreseen that the following combinations of forward and reverse primer are preferred: forward primer according to SEQ ID NO:2 with reverse primer according to SEQ ID NO:3; forward primer according to SEQ ID NO:4 with reverse primer according to SEQ ID NO:5; forward primer according to SEQ ID NO:6 with reverse primer according to SEQ ID NO:7.

In a particular preferred embodiment of the invention, the combination is forward primer according to SEQ ID NO:2 with reverse primer according to SEQ ID NO:3.

In a preferred embodiment of the present invention, it is foreseen that the PCR is preferably real-time PCR, end-point PCR; end-point PCR with fluorescence detection, quantitative PCR, digital PCR, open-array PCR, digital drop PCR, quantitative digital PCR, quantitative real-time PCR, PCR suitable for high-throughput, and microarrays.

Preferably, the method according to the present invention is conducted in high-through put format. It is an advantage of the present invention that the PCR can be conducted in greater approach with numerous single assays in parallel. Thus, it is possible to conduct up to 200000 reactions per day in form of a high-throughput approach and respective automatization with the method of the present invention. In a further preferred embodiment of the present invention, a film is used as material for conducting the PCR procedure. Advantageously, using of a film allows conducting the method of the present invention in a small reaction volume. Preferably, the PCR is conducted with a reaction volume of 25 nL to 50 µL.

Therefore, in the case of conducting of the method according to the present invention in an extreme high-throughput format, which may comprise the analysis of about 200,000 eggs in 24 h, it is an application of a fast and very safe real time read out system. Anyway it is an essential prerequisite to gain results about the sex of the chicken to a maximum of reliability and certainty. The required accuracy of the prediction must exceed 95%. The mortality of the embryo due to the invasive determination must be less than 5%. This is necessary, in view of the business conditions in the field of hatchery including an extreme high time and cost pressure. Therefore, it is mandatory that the highest sensitivity, productivity and specificity are maintained, and that the results obtained are correct at the first time, since a repetition of the method can hardly be performed. Advantageously, the method of the present invention is able to provide such reliable and highly correct results in high-throughput format which is in particular achieved by the use of a target sequence having a size in the range of preferably 60 by to 160 bp.

Preferably, it is foreseen to use different fluorescence detection systems or fluorescence read-out devices for the detection of the PCR products. In a further preferred embodiment of the invention, PCR is conducted and lateral flow devices are used for the detection of the PCR products. In a particularly preferred embodiment of the present invention, visual detection of PCR products with gold nanoparticles and a nucleic acid lateral flow (NALF) device is foreseen. In a further preferred embodiment, the PCR can be conducted in a water bath.

In a further preferred embodiment of the method of the invention, it is foreseen that additionally to the steps of claim 1 a further PCR is conducted, wherein said further PCR comprises the following steps of: (a') providing a nucleic acid sequence from the biological sample, (b') amplifying and detecting at least one target sequence specific for the HKG gene of Gallus, wherein a forward primer according to SEQ ID NO:10 and a reverse primer according to SEQ ID NO:11 is used.

The additional HKG represents the determination of the House Keeping Gene (HKG) for Gallus. This assay allows the determination of the respective HKG DNA in male and female chicken samples. This assay therefore allows determining if the sample is a male chicken, or if the sample does not contain sufficient DNA for a successful conduction of the PCR. Accordingly, this HKG PCR represents also a control of the conduction of the PCR in combination with the W chromosome PCR. It allows the decision if the egg from which the sample has been taken should be further incubated, since it will generate a female chicken, or if this egg may be discarded if it will generate a male chicken.

Preferably, it is foreseen that the PCR specific for the HKG gene is conducted together with the PCR specific for the W chromosome.

In a further preferred embodiment of the present invention, the amplifying and detecting in step (b) comprises using a probe comprising an oligonucleotide of between 10 and 40 nucleotides in length and of at least 10 contiguous nucleotides of a nucleotide sequence located in the range of nucleotide 46 to 446 of SEQ ID NO:1, wherein the probe comprises a fluorophore dye and/or a quencher.

The use of a probe is in particular preferred in the case the method of the present invention is conducted as real-time PCR. In a further preferred embodiment of the invention an end-point PCR with fluorescence detection is conducted. The use of a probe may be also preferred with further PCR methods known to those skilled in the art.

Preferably, the probe is selected from the group consisting of SEQ ID NO: 12, 13, 14, and 15.

In a further preferred embodiment of the present invention, step (b') is also conducted comprising using a probe. Preferably, the probe is according to SEQ ID NO:16. In a further preferred embodiment the probe as used in step (b') comprises a fluorophore dye and/or quencher.

In a further preferred embodiment, a probe is used comprising a minor groove binder, which represents a distinct chemical modification of the probe allowing the binding of probes of shorter length, in combination with a fluorophore dye and/or a quencher.

In a further preferred embodiment of the invention, the fluorescence dye and quencher are selected from the group consisting of 6-Fam, Fluorescein, Hex, joe, vic, TET, BHQ1, Tamra, OQA, Texas Red, Rox, Cy5, Cy5.5, Atto680, BHQ2, BHQ3, OQB, OQC, OQD, NED, CALFluorGold540, CALFluorOrange560, CALFluorRed590, Cy3, Cy3.5, Yakima Yellow, Quasar570, Quasar670, AlexaFluor350, ATTO425/532, ATTO425/532, ATTO550, ATTO620, ATTO680, ATTO647N, Dyonics681, and MGB.

In a preferred embodiment of the present invention, the following fluorescence combinations are preferred 6-FAM with BHQ1, Texas Red with BHQ2.

According to the present invention, it is preferably foreseen that the biological sample is egg white, preferably from allantois, feathers, egg fluid, chicken embryonal cells, chicken embryo material, yolk, any biological material of the egg and or developing chicken embryo.

In particular it is foreseen that the biological sample of the present invention can be genetic material of chicken, such as DNA or RNA.

In a further preferred embodiment of the present invention, it is foreseen that the forward primer and/or the reverse primer have a 5' or 3'-modification. A particularly preferred modification is a Twisted Intercallating Nucleic Acid (TINA) modification. This modification can improve the primer stability during the PCR.

Preferably, the method of the present invention is conducted according to the following: amplifying in step (b) is conducted according to the following parameters: Step 1: 94-98° C. for 1-20 min; Step 2: 94-98° C. for 5-15 sec; Step 3: 55-65° C. for 5-60 sec, optionally back to Step 2 for 30-50 cycles, then detecting the results (as 2 Step PCR); if Step 2 is not conducted than Step 4: 68-76° C. for 5-60 sec, back to Step 2 for 30-50 cycles, then detecting the results (as 3 Step PCR).

The method according to the present invention has distinct advantages compared to the methods of the prior art. The method is conducted as real-time PCR, which method allows a robust, reliable and fast read out system for parts of the method, namely the detection of the W chromosome—W chromosome assay—and preferably also of a house keeping gene (HKG) of Gallus domesticus—HKG assay. The method according to the present invention allows high throughput analysis. Both PCR reactions can be conducted together in one single reaction.

Preferably, the fluorescence dyes according to the method of the present invention are such that the different fluorescence absorption maxima do not interact with each other. Therefore, the signal of the detection of the W chromosome and the signal of the HKG assay do not influence each other. This is in particular achieved such that preferably the reporter and quencher dyes are selected to be compatible to each other to achieve good results for the W chromosome assay and the HKG assay.

The method of the present invention does not require that any analyses of PCR amplified fragments have to be conducted, such as analyses of fragments from gel electrophoresis, capillary electrophoresis or melting curve analysis.

Both assays, the W chromosome assay and the house keeping gene assay, elicit a coherent amplification course with a maximum deviation of +−3.4 cycles.

A further advantage of the method of the present invention is that this method represents a reliable molecular biological differentiation of the sex in chicken within also of low concentrated DNA contents of the biological sample which has to be investigated. Moreover, in case the method of the present invention is conducted as an assay wherein the detection of the W chromosome is combined with the detection of the HKG gene, then a differentiation between samples containing not enough DNA or insufficient DNA on the one hand side and the presence of a male chicken on the other hand side is possible.

According to the method of the present invention, it is possible to achieve a rate of 96.6% of correctly determined female chicken in the analysed biological samples. It has to be noted, that it is not possible to achieve such a very positive rate with any of the methods of the prior art.

The method of the present invention allows a reliable and unambiguous distinction of unhatched female and male chicks based on the egg fluid or the respective biological sample used.

The method of the present invention allows the detection of already 1 to 2 copies of chicken chromosomal W-DNA and 1 to 2 copies chicken DNA in a concentration dependent PCR-Assay (W-assay).

The sensitivity of the method of the present invention is very high which is also the result of very short amplification length of the PCR products of only 60 to 300 bp, the fact that no degenerated bases are used in the primer and probes sequences, and the fact that no unspecific amplification occurs up to 50 cycles of the PCR.

Therefore, the method of the present invention provides linearity of the detection in the range of 3 to 10000 template copies. The efficiency of the PCR according to the present invention is very good and lies in the range of about 100%.

A further subject-matter of the present invention relates to a kit for determining the presence or absence of at least one nucleic acid sequence specific for the sex of chicken in a biological sample, the kit comprising: a forward primer and a reverse primer each comprises an oligonucleotide of between 10 and 30 nucleotides in length and of at least 10 contiguous nucleotides of a nucleotide sequence located in the range of nucleotide 46 to 446 of SEQ ID NO:1.

In a preferred embodiment of the invention, the kit comprises also a probe which comprises a oligonucleotide of between 15 to 40 oligonucleotides in length and at least 15 contiguous nucleotides of a nucleotide sequence located in the range of nucleotide 46 to 446 of SEQ ID NO:1.

According to the present invention, it is preferably foreseen that the kit may comprise one or more of the following components: a microtiter plate, PCR reaction mix, and amplification buffers.

In a preferred embodiment of the present invention, the kit foresees that the forward primer is selected from the group consisting of SEQ ID NO: 2, 4, 6, and 8, and the reverse primer is selected from the group consisting of SEQ ID NO: 3, 5, 7, and 9.

In a preferred embodiment of the invention, kit further comprises a probe. Further preferred it is foreseen that the probe is useful in the detection of the W chromosome and/or in the detection of the HKG. Preferably, the probe is selected of the group consisting of SEQ ID NO: 12, 13, 14, and 15 for the W chromosome assay, and preferably SEQ ID NO: 16 for the HKG assay.

A further subject-matter of the claims is directed to a pair of oligonucleotides for the amplification of at least one nucleic acid sequence specific for the sex of chicken in a biological sample comprising a first oligonucleotide of between 10 and 30 nucleotides in length and of at least 10 contiguous nucleotides of a nucleotide sequence located in the range of nucleotide 46 to 446 of SEQ ID NO:1, and a second oligonucleotide of between 10 and 30 nucleotides in length and of at least 10 contiguous nucleotides of a nucleotide sequence located in the range of nucleotide 46 to 446 of SEQ ID NO:1.

In a preferred embodiment of the present invention, it is foreseen that the first oligonucleotide is selected from the group consisting of SEQ ID NO:2, 4, 6, and 8, and the second oligonucleotide is selected from the group consisting of SEQ ID NO:3, 5, 7, and 9.

In a preferred embodiment of the present invention, it is foreseen that the pair of isolated oligonucleotides are the preferred combination, wherein the first oligonucleotide is SEQ ID NO:4 and the second oligonucleotide is SEQ ID NO:5, further preferred wherein the first oligonucleotide is SEQ ID NO:6 and the second oligonucleotide is SEQ ID NO:7, in particular preferred wherein the first oligonucleotide is SEQ ID NO:2 and the second oligonucleotide is SEQ ID NO:3.

The invention is further described with the following examples. The content of these examples should not be understood as limiting, but as illustrative embodiments of the present invention.

EXAMPLE 1

PCR Methods According to the Prior Art

Comparative real-time PCR analyses have been conducted with subsequent HRMA (high resolution melting curves analysis) to determine the following parameters: Sensitivity, limit of detection, linearity, cross-reactivity, melting temperatures, performance in a duplex assay, arising of false positive signals and a coherence of the amplification between HKG and W chromosome detection. Female and male chicken DNA has been used as template at a concentration of ≤1.2 pg to 5 ng.

The following assays using primers specific for chicken W chromosome as described in the prior art have been found to be unacceptable in view of the above-mentioned parameters.

A PCR has been conducted based on the primers as disclosed in Rosenthal et al., 2010 Poultry Science 89: 1451-1456. This assay has been conducted with the designation pmCHD1-Z-Sh for determination of the Z chromosome and with the designation pmCHD1-W-Sh for the determination of the W chromosome. However, it could be shown that this assay is not suitable to allow a reliable sex determination since this assay showed an up to four-fold weaker amplification of the male chicken DNA compared to the female chicken DNA. Further, the pmCHD1-W-Sh assay should to be not appropriate for the determination in view of the above-mentioned required parameters. This assay showed that cross-reactivity occurred arising from the male chicken DNA and false positive signals have been noticed. Moreover, this assay did not allow to perform an additionally HKG assay.

A further PCR has been conducted according to the primers as disclosed in Aun and Kumaran, Pertanika J. Trop. Agric. Sci. 33 (2): 329-336, 2010. This assay has been performed with the designation pmP2P8-CHDWZ for the determination of W and Z chromosome. This assay did not allow the additionally conducting of a HKG assay. Therefore, this assay is not suitable to be part of a duplex assay. A further PCR assay on the basis of the publication of Aun and Kumaran, 2010 has been performed with the designations pmJVG-GGW for the detection of the W chromosome and pmJVG-GGZ for the determination of the Z chromosome. The pmJVG-GGW assay did not allow a reliable detection of the W chromosome. The amplification rate of this assay is very weak. Further cross reactivity has been observed arising from male chicken DNA and false positive signals occurred. Moreover, the detection of the W chromosome has not been possible in case of only 1 to 3 copies of chicken DNA in the biological sample.

In summary, none of the primers described in the prior art allowed to establish a reliable PCR assay to provide a definite and unambiguous determination of the W chromosome in chicken DNA. Therefore, a suitable discrimination of the sex is not possible on the basis of the primers described in the prior art.

EXAMPLE 2

Conducting Real-Time PCR According to the Method of the Invention

A duplex assay has been performed for the detection of the W chromosome and HKG as control assay. The designation of this assay has been pmGGW-76-TxRed. The aim of this duplex assay is the determination of the W chromosome (W-assay) as one part of the duplex assay and of a house-keeping gene of Gallus (HKG assay) as the second part of the duplex assay.

In a first step, DNA has been extracted from egg fluid at day 3 of the breed of the eggs. PCR has been conducted with the following parameters:

A qPCR mix has been generated:
qPCR Mix
2-5× master mix comprising buffer, polymerase, dNTPs, $Mg^{2+}$
$Mg^{2+}$: 1-6 mM per reaction
dNTPs: 50-800 µM each per reaction
oligonucleotides: 50-500 nM per reaction
probes: 50-500 nM per reaction
template: 1 to 100000 copies
The PCR conditions provide the following characteristics:
Hotstart polymerase with 5' to 3' polymerisation and exonuclease activity, but without 3' to 5' exonuclease activity (proof reading): for TaqMan system; use at room temperature
Without Rox as reference dye in the enzyme mix: allows analysis at the emission range of Texas Red reporter dye
Use of the following dNTPs: dATP, dCTP, dGTP, dTTP. A higher reaction sensitivity and efficiency is given in view of dUTP.
Thus, no use of uracil DNA glycoside (UDG)
Optional: 0.5-3% DMSO or 0.5-3% formamide
PCR Reaction
Step 1:94-98° C. for 1-20 min
Step 2:94-98° C. for 5-15 sec
Step 3: 55-65° C. for 5-60 sec, back to Step 2 for 30-50 cycles, then read out of the results Mandatory:
Step 4: 68-76° C. for 5-60 sec, back to Step 2 for 30-50 cycles, then read out of the results Optional: read out of the results in case an endpoint PCR is conducted
Primer
GC content: 40-80%
Melting temperature Tm: 58-80° C.
Length of the oligonucleotides: 15-30 bp
No degenerated bases are used
Optional: modification at the 5'-end: Twisted Intercallating Nucleic Acid: TINA (Eurofins)

Probes
Dual-labeled probes have been used
GC content: 40-80%
Melting temperature Tm: 59-75%
Length of the probes: 15-40 bp
Modification of probe 1 at the 5'-end: 6-Fam, Fluoresceine, Hex, Joe, Vic, TET
Modification of probe 1 at the 3'-end: BHQ1, Tamra, OQA
Modification of probe 2 at the 5'-end: Texas Red, Rox, Tamra, Cy5, Cy5.5, Atto680
Modification of probe 2 at the 3'-end: BHQ2, BHQ3, OQB, OBC, OQD
The results of the real-time PCR are depicted in the corresponding figures.

FIG. 1 shows SEQ ID NO:1 representing the chicken W chromosome fragment. Underlined with a black line is the range of nucleotide 46 to 446. In this range are the preferred primers and probes are located which provide the advantageous conduction of the method of the present invention.

FIG. 2 shows the result of a real time PCR. Depicted is male chicken DNA in different concentrations. The male DNA is shown in the channels depicted with the dotted line and represent positive signal for HKG. No signals can be observed in the channel depicted with the straight dark line which represent signal for the W chromosome.

Figure 3:
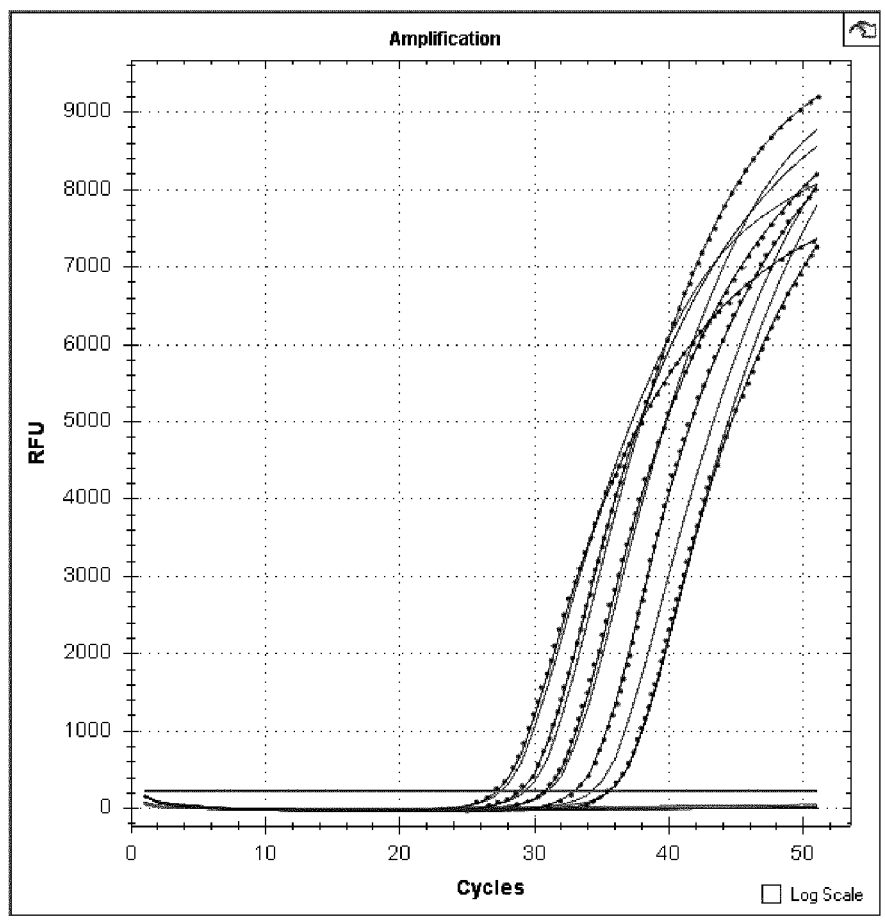
FIG. 3 shows the result of a real-time PCR. Female chicken DNA is depicted in different concentrations.

FIG. 3 shows the result of a real-time PCR. Female chicken DNA is depicted in different concentrations. Signals are shown in the channel with the dotted line which represents HKG signals. The channel with the straight dark line represents signals of the W chromosome.

In FIGS. 2 and 3 is also shown that the negative controls and the "none template" controls are on background level under the threshold.

Figure 4:
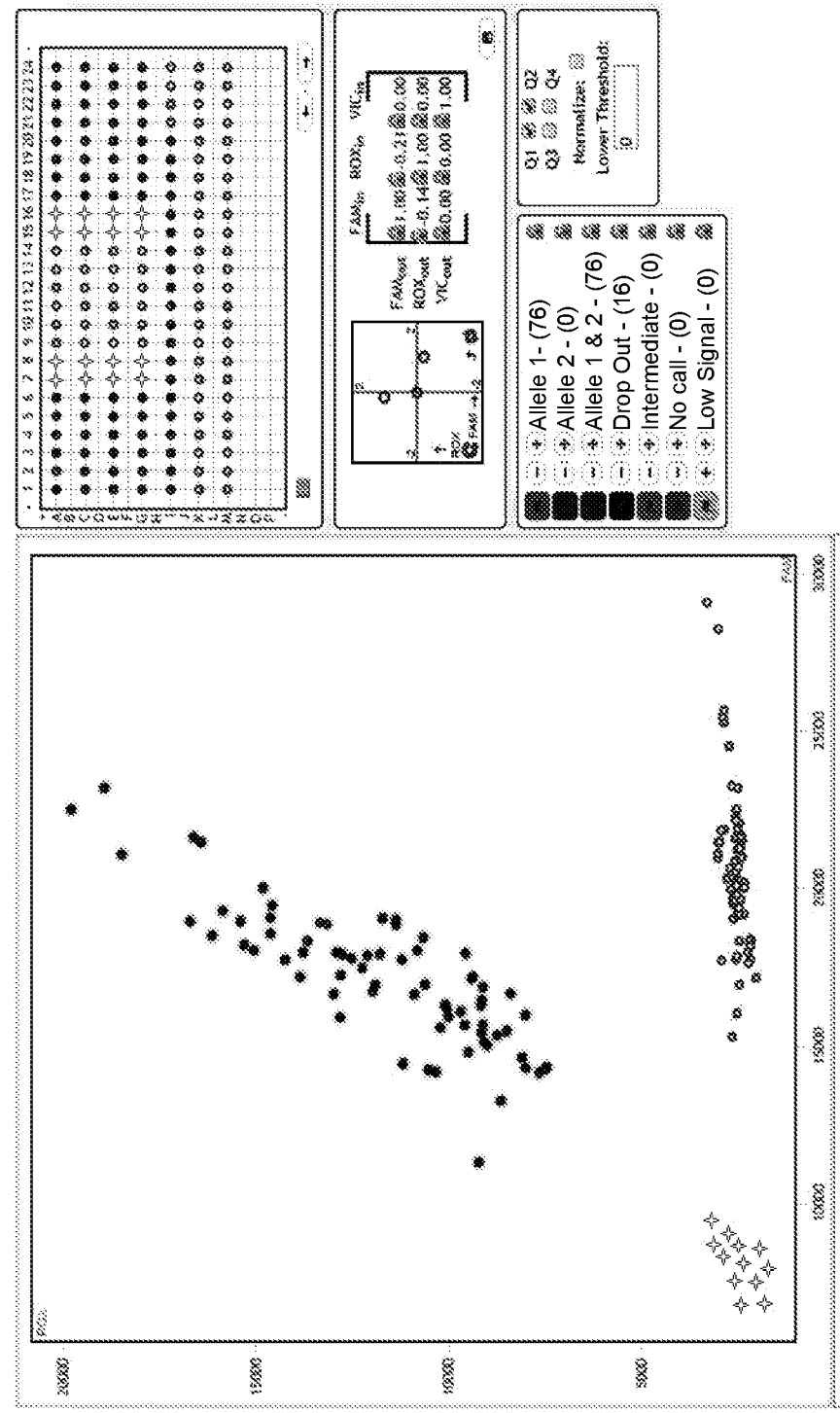
FIG. 4 shows the results of an endpoint PCR with fluorescence detection and provides an example for the high-throughput analysis.

FIG. 4 shows the results of an endpoint PCR with fluorescence detection. The dots with star form represent negative controls and "none template" controls. The dots with white background represent male chicken DNA in different concentrations. The black dots represent female DNA in different concentrations. In the upper right of FIG. 4 a representative microtiter plate is depicted showing the result of single samples. In the middle and at the bottom of the right side of FIG. 4 setting interpretations of the fluorescence channels are shown.

Preferred primers and probes used in this example are:
W assay
Forward primer: according to SEQ ID NO:2
Reverse primer: according to SEQ ID NO:3
Probe: according to SEQ ID NO:12
HKG assay
Forward primer: according to SEQ ID NO: 10
Reverse Primer: according to SEQ ID NO:11
Probe: according to SEQ ID NO:16

Preferably, the probe of the W chromosome assay is modified with Texas Red, and the probe of the HKG assay is modified with FAM in combination with BHQ1.

The duplex assay according to the present invention provides the following advantages. The W chromosome determination does not show any cross reactivity in view of the male chicken DNA up to 50 PCR cycles. HKG is amplified with the same efficiency from male and female chicken DNA. Both parts of the assay possess the same efficiency of the PCR, are dependent on concentration and are linear with an analytic limit of detection of <3 copies of the genome.

It could be shown that both assays show no false-positive signals up to 50 PCR cycles. The PCR products detection has been conducted also by using a respective probe.

The invention claimed is:

1. A high throughput detection method for the detection of the presence or absence of at least one nucleic acid sequence specific for the sex of a chicken in a biological sample from the chicken using polymerase chain reaction (PCR), wherein the method comprises the following steps of:
   (a) providing the biological sample,
   (b) amplifying at least one target sequence specific for the sex of chicken using PCR in the biological sample, wherein a forward primer and a reverse primer is used, wherein the forward primer is selected from the group consisting of SEQ ID NO: 2, 4, 6, and 8 and the reverse primer is selected from the group consisting of SEQ ID NO: 3, 5, 7, and 9, and wherein the target sequence has a size in the range of 60 bp to 160 bp, and
   (c) detecting the amplification product of step (b) using a probe comprising an oligonucleotide of between 15 and 40 nucleotides in length and of at least 15 contiguous nucleotides of a nucleotide sequence located in the range of nucleotide 46 to 446 of SEQ ID NO:1, wherein the probe comprises a fluorophore dye and/or a quencher,
wherein the nucleic acid sequence specific for the sex of chicken is a sequence of the W chromosome of chicken, and wherein said method can detect 1 to 3 copies of said target sequence.

2. The method according to claim 1, wherein the target sequence has a size in the range of 70 bp to 160 bp.

3. The method of claim 2, wherein the target sequence has a size in the range of 75 bp to 155 bp.

4. The method of claim 2, wherein the target sequence has a size in the range of 75 bp to 140 bp.

5. The method of claim 2, wherein the target sequence has a size in the range of 75 bp to 120 bp.

6. The method of claim 2, wherein the target sequence has a size in the range of 75 bp to 100 bp.

7. The method of claim 2, wherein the target sequence has a size of 76 bp.

8. The method according to claim 1, wherein the PCR is real-time PCR, end-point PCR; end-point PCR with fluorescence detection, quantitative PCR, digital PCR, open-array PCR, digital drop PCR, quantitative digital PCR, quantitative real-time PCR, PCR suitable for high-throughput, and microarrays.

9. The method of claim 1, wherein additionally to the steps of claim 1 a further PCR is conducted, wherein said further PCR comprises the following steps of:
   (a') providing a nucleic acid sequence from the biological sample,
   (b') amplifying and detecting at least one target sequence specific for the HKG gene of Gallus,
wherein a forward primer according to SEQ ID NO: 10 and a reverse primer according to SEQ ID NO: 11 is used.

10. The method according to claim 9, wherein the PCR specific for the HKG gene is conducted together with the PCR specific for the W chromosome.

11. The method according to claim 1, wherein the probe is selected from the group consisting of SEQ ID NO:12, 13, 14, and 15.

12. The method according to claim 1, wherein the fluorphore dye and quencher are selected from the group consisting of 6-Fam, Fluorescein, Hex, joe, vic, TET, BHQ1, Tamra, OQA, Texas Red, Rox, Cy5, Cy5.5, Atto680, BHQ2, BHQ3, OQB, OQC, OQD, NED, CALFluorGold540, CALFluorOrange560, CALFluorRed590, Cy3, Cy3.5, Yakima Yellow, Quasar570, Quasar670, AlexaFluor350, ATTO425/532, ATTO425/532, ATTO550, ATTO620, ATTO680, ATTO647N, Dyonics681, and MGB.

13. The method according to claim 1, wherein the biological sample is egg white, feathers, egg fluid, chicken embryonal cells, chicken embryo material, yolk, any biological material of the egg and or developing chicken embryo.

14. The method according to claim 1, wherein the forward primer and/or the reverse primer have a 5' or 3'-modification.

15. The method according to claim 1, wherein amplifying in step (b) is conducted according to the following parameters:
   Step 1: 94-98° C. for 1-20 min;
   Step 2: 94-98° C. for 5-15 sec;
   Step 3: 55-65° C. for 5-60 sec,
   then detecting the results.

16. The method according to claim 1, wherein amplifying in step (b) is conducted according to the following parameters:
   Step 1: 94-98° C. for 1-20 min;
   Step 2: 94-98° C. for 5-15 sec;
   Step 3a: 55-65° C. for 5-60 sec;
   Step 3b: 94-98° C. for 5-15 sec for 30-50 cycles,
   Step 4a: 68-74° C. for 5-60 sec,
   Step 4b: 94-98° C. for 5-15 sec for 30-50 cycles,
   then detecting the results.

17. A kit for determining the presence or absence of at least one nucleic acid sequence specific for the sex of chicken in a biological sample, the kit comprising:
   a forward primer and a reverse primer wherein the forward primer is selected from the group consisting of SEQ ID NO:2, 4, 6, and 8, and the reverse primer is selected from the group consisting of SEQ ID NO:3, 5, 7, and 9,
wherein the forward and reverse primers amplify a target sequence in the range of 60 bp to 160 bp, and
  a probe comprising an oligonucleotide of between 15 and 40 nucleotides in length and at least 15 contiguous nucleotides of a nucleotide sequences located in the range of nucleotides 46 to 446 of SEQ ID NO: 1,
wherein the probe comprises a fluorophore dye and/or a quencher.

18. A pair of oligonucleotides and a probe for the amplification and detection of at least one nucleic acid sequence specific for the sex of chicken in a biological sample comprising:
  a first oligonucleotide is selected from the group consisting of SEQ ID NO:2, 4, 6, and 8, and
  a second oligonucleotide is selected from the group consisting of SEQ ID NO:3, 5, 7, and 9,
wherein the first and second oligonucleotide amplify a target sequence in the range of about 60 bp to 160 bp, and
  a probe comprising an oligonucleotide of between 15 and 40 nucleotides in length and at least 15 contiguous nucleotides of a nucleotide sequences located in the range of nucleotides 46 to 446 of SEQ ID NO: 1,
wherein the probe comprises a fluorophore dye and/or a quencher.

19. The pair of isolated oligonucleotides according to claim 18, wherein the first oligonucleotide is SEQ ID NO:4 and the second oligonucleotide is SEQ ID NO:5.

20. The pair of isolated oligonucleotides according to claim 19, wherein wherein the first oligonucleotide is SEQ ID NO:6 and the second oligonucleotide is SEQ ID NO:7.

21. The pair of isolated oligonucleotides according to claim 19, wherein the first oligonucleotide is SEQ ID NO:2 and the second oligonucleotide is SEQ ID NO:3.

* * * * *

UNITED STATES PATENT AND TRADEMARK OFFICE
CERTIFICATE OF CORRECTION

PATENT NO. : 10,711,305 B2
APPLICATION NO. : 15/772842
DATED : July 14, 2020
INVENTOR(S) : Weigel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 60 days.

Signed and Sealed this
Fourteenth Day of February, 2023

*Katherine Kelly Vidal*

Katherine Kelly Vidal
*Director of the United States Patent and Trademark Office*